United States Patent [19]

Burgfels et al.

[11] Patent Number: 5,063,187

[45] Date of Patent: Nov. 5, 1991

[54] CATALYST BASED ON CRYSTALLINE ALUMINOSILICATE

[75] Inventors: Götz Burgfels, Feilenbach-Au; Karl Kochloefl, Bruckmühl; Jürgen Ladebeck, Bad Aibling; Friedrich Schmidt, Rosenheim; Michael Schneider, Ottobrunn/Riemerling; Hans J. Wernicke, Geretsried, all of Fed. Rep. of Germany

[73] Assignee: Sud-Chemie Aktingesellschaft, Munich, Fed. Rep. of Germany

[21] Appl. No.: 436,477

[22] Filed: Nov. 14, 1989

[30] Foreign Application Priority Data

Nov. 15, 1988 [DE] Fed. Rep. of Germany ....... 3838710

[51] Int. Cl.$^5$ .............................................. B01J 29/28
[52] U.S. Cl. ......................................... 502/71; 502/62
[58] Field of Search .............................. 502/62, 64, 71

[56] References Cited

U.S. PATENT DOCUMENTS

| | | | |
|---|---|---|---|
| 4,164,482 | 8/1979 | Berger et al. | 502/62 |
| 4,631,267 | 12/1986 | Lachman et al. | 502/64 |
| 4,900,529 | 2/1990 | Sanchez et al. | 502/71 |

*Primary Examiner*—Carl F. Dees
*Attorney, Agent, or Firm*—Herbert P. Price

[57] ABSTRACT

A catalyst based on crystalline aluminosilicates of the pentasil type, having an Si/Al atomic ratio of at least 10, has the structure of primary crystallites of a mean diameter of at least 0.1 micron and at most 0.9 micron, which crystallites are partially combined into agglomerates the primary crystallites and/or agglomerates being mutually joined by finely disperse alumina obtainable by hydrolysis of aluminum-organic compounds, the BET surface area of the catalyst being 300 to 600 m$^2$/g and its pore volume (determined by mercury porosimetry) being 0.3 to 0.8 cm$^3$/g.

19 Claims, No Drawings

CATALYST BASED ON CRYSTALLINE ALUMINOSILICATE

BACKGROUND OF THE INVENTION

The field of art to which this invention pertains is catalysts and their supports.

Catalysts based on crystalline aluminosilicates which are prepared from a source of aluminum, a source of silicon, a source of alkali, a template (for example a tetrapropylammonium compound) and water, are known from U.S. Pat. No. 3,702,886. Depending on the composition of the starting mixture, the size of the primary crystallites is 1 micron or less. It was not realized that the size of the primary crystallites must not fall below a defined limit. Binders can be used for agglomerating primary crystallites, but no data are given on the size of the agglomerates and alumina is not mentioned as a binder. Neither are there any data on the particle size of the binder. If bentonite is used as the binder, the catalysts have an unfavorable pore distribution and a shorter life.

West German Patent No. DE 2,822,725 has disclosed the preparation of methanol conversion catalysts based on crystalline aluminosilicates. The diameter of the primary crystallites is 1 micron and greater. The object is the preparation of primary crystallites having diameters of much more than 1 micron. For this purpose, the crystal growth must be promoted by higher temperatures, and nucleation must be inhibited by low concentrations of the templates essential to the crystallization of the zeolites. Moreover, there are no references to the use of binders or to the size of the agglomerates.

According to West German Patent No. DE 2,405,909, the catalysts for hydrocarbon conversion are prepared on the basis of zeolites of the ZSM-5 type, the mean diameters of the primary crystallites being in the range from 0.05 to 0.1 micron. In this way, aging of the catalysts is to be delayed. The small primary crystallites, produced by setting a high stirrer speed, are difficult to filter off. Agglomerates of the order of size of 0.1 to 1 micron are produced from the primary crystallites. To prepare the catalysts, alumina as a binder is, inter alia, added to the agglomerates, other binders also being mentioned as equivalent. There are no data on the particle size of the agglomerates in the finished catalysts or of the binders. Moreover, the synthesis was carried out in the presence of sulfuric acid, using $Al_2(SO_4)_3 \cdot xH_2O$.

According to West German Patent No. DE-2,935,123, ZSM-5 or ZSM-11 zeolites are prepared with the use of ammonium hydroxide and an alcohol as the template, the presence of seeds being the distinctive feature. The zeolites are used as cracking and hydrocracking catalysts and also as catalysts for isomerization and dewaxing. Alumina can be used as a binder. There are no data, however, on the size of the primary crystallites or of the agglomerates and the binder.

A process for the preparation of zeolites and their use as catalysts for the conversion of aliphatic compounds into aromatic hydrocarbons is described in West German Patent No. DE-2,913,552. The template used is a mixture of butanol and ammonium hydroxide. The size of the primary crystallites is said to be less than 3 microns, preferably less than 2 microns. No lower limit is given. Alumina can, inter alia, be used as a binder for the agglomerates, but no particle sizes are given for the agglomerates and the binder.

West German Patent No. DE-3,537,459 has disclosed a process for the preparation of large, evenly shaped crystals of zeolites of the pentasil type from $SiO_2$ and a compound of one or more trivalent elements, such as Al, B, Fe, Ga or Cr in amine-containing solutions, which comprises using fumed $SiO_2$ produced by combustion of a silicon chloride as the $SiO_2$-containing starting material. The zeolites are used for the conversion of organic compounds, in particular for the conversion of methanol to hydrocarbons which contain lower olefins and aromatics. The zeolites obtained are not intergrown into agglomerates.

European Patent No. EP-173,901 relates to a process for the preparation of small zeolite crystallites of the ZSM-5 type having an $SiO_2/Al_2O_3$ molar ratio of more than 5, corresponding to an Si/Al atomic ratio of more than 2.5. The smallest dimension of the crystallites is less than 0.3 micron. The crystallites are subjected to an ion exchange reaction and, after mixing with a matrix material, are molded into larger particles. These are dried and calcined, catalysts for various hydrocarbon conversion reactions being obtained. There are no data on the nature and the effect of the matrix material.

European Patent No. EP-123,449 describes a process for converting alcohol or ethers into olefins, using steam-treated zeolite catalysts; the latter have a crystal size of less than 1 micron and can be incorporated into a matrix. Clays, silica and/or metal oxides are mentioned as matrix materials.

U.S. Pat. No. 4,206,085 relates to hydrocarbon conversion catalysts based on zeolites and a matrix material, for increasing the abrasion resistance. The matrix material used is alumina from pseudoboehmite, and $SiO_2$ from ammonium polysilicate or silica sol. The preferred zeolite is of the faujasite type. There are no data on the size of the zeolite crystals.

SUMMARY OF THE INVENTION

This invention relates to catalysts based on crystalline aluminosilicates of the pentasil type having an Si/Al atomic ratio of at least 10. These catalysts have an improved service life and an increased activity and selectivity in catalytic processes, in particular in methanol conversion processes and olefin oligomerization processes.

These catalysts are defined by a structure of primary crystallites of a mean diameter of at least about 0.1 micron and at most about 0.9 micron which crystallites are partially combined into agglomerates, the primary crystallites and/or agglomerates being mutually joined by finely divided alumina obtainable by hydrolysis of aluminum-organic compounds, the BET surface area of the catalysts being about 300 to about 600 $m^2/g$ and their pore volume (determined by mercury porosimetry) being about 0.3 to about 0.8 $cm^3/g$.

If the primary crystallites are partially combined into agglomerates, they are only loosely bound to one another as, for example, in filter cakes. From the latter, the primary crystallites can be recovered relatively easily, for example, by dispersing the filter cake in an aqueous medium and by stirring the dispersion.

All the parameters indicated above are essential for obtaining catalysts having a high activity, selectivity and a long life.

DESCRIPTION OF THE INVENTION

It is important that in the catalysts of this invention the primary crystallites have a mean diameter of at least about 0.1 micron and at most about 0.9 micron. Preferably, the mean diameter of the primary crystallites is in the range from 0.1 to 0.6 micron. If the mean diameter is less than 0.1 micron the service life of the catalysts is considerably shortened whereas, at a diameter of more than 0.9 micron, the initial activity is very low. The mean diameter of the primary crystallites is defined as the arithmetic mean, averaged over a large number of crystallites, between the largest and the smallest diameter of an individual crystallite. This definition is of importance in the case of crystallites of an irregular crystal shape, for example rod-shaped crystallites. In the case of spherical or approximately spherical crystallites, the largest and the smallest diameters coincide.

In the catalysts according to the invention, at least 20 percent of the primary crystallites can be combined into agglomerates of about 5 to about 500 microns. The values given are again the mean dimensions (arithmetic mean of the largest and smallest dimensions, averaged over a large number of crystallites).

The primary crystallites and/or the agglomerates are mutually joined by finely divided alumina which is obtainable by hydrolysis of aluminum-organic compounds.

The joined particles have, in general, dimensions of from about 20 to about 1000 microns, in particular from about 50 to about 800 microns. These values are again mean dimensions, defined as indicated above.

The structure of the catalyst, comprising primary crystallites, agglomerates and binder particles, also determines the BET surface area (300 to 600 m$^2$/g), the pore volume (0.3 to 0.8 cm$^2$/g) and the pore diameter, i.e. at least 60 percent of the pores have, preferably, a diameter of from 14 to 90 nm.

The BET surface area, the pore volume and the pore diameter represent an optimized selection for obtaining catalysts having a high activity, selectivity and a long life.

The quantity of the finely divided alumina binder is preferably 10 to 40 percent by weight, relative to the weight of the end product.

Preferably, the finely divided alumina binder in the reaction batch is in the form of peptizable hydrated alumina, at least 95 percent (relative to the mean diameter) of the particles thereof being $\leq 55$ microns. The finely divided alumina binder can be made by hydrolysis of aluminum trialkyls or aluminum alkoxides.

The catalyst according to the invention is obtainable preferably in the following manner:

(a) in an aqueous reaction batch containing a source of silicon, a source of aluminum, a source of alkali and a template, an alkaline aluminosilicate gel is produced in a manner known per se (as described in U.S. Pat. No. 3,702,886 which is hereby incorporated by reference), at an elevated temperature and, if appropriate, under an elevated pressure and converted to a crystalline aluminosilicate, but the reaction being stopped when the primary crystallites obtained have a mean diameter of at least about 0.1 micron and at most about 0.9 micron, preferably 0.1 to 0.6 micron;

(b) the primary crystallites are separated as pre-agglomerates from the aqueous reaction medium, dried and subjected to an intermediate calcination;

(c) the product from stage (b) is reacted in an aqueous medium with a substance containing protons or donating protons on heating, for the purpose of exchanging the alkali metal ions, is separated off, dried and once more subjected to an intermediate calcination, whereupon an agglomerate fraction of about 5 to 500 microns is separated off;

(d) the agglomerate fraction from stage (c) is mixed with the finely divided hydrated alumina; and (e) the product from stage (d) is subjected to a final calcination.

The importance of the individual stages, by means of which the catalyst according to the invention is obtainable is explained in more detail below:

In stage (a), an aqueous reaction batch containing a source of silicon (for example colloidal silica or an alkali metal silicate), a source of aluminum (for example aluminum hydroxide or sodium hydroxide, it being possible for the source of alkali also to be apart of the source of silicon if alkali metal silicates are used, and to be part of the source of aluminum if alkali metal aluminates are used) and a template is first prepared. The proportions by weight between the source of silicon and the source of aluminum are selected such that crystalline aluminosilicates having an Si/Al atomic ratio of at least 10, preferably of about 20 to about 500:1, are obtained. An alkaline aluminosilicate gel is produced from the reaction batch at an elevated temperature and, if appropriate, under an elevated pressure in an manner known per se. This can be done at temperatures of about 90° C. but in this case the reaction times become relatively long (about 1 week). The process is therefore preferably carried out at temperatures from 90° C. to about 190° C., in particular from 90° C. to 150° C., a positive pressure being established automatically at temperatures of more than 100° C. (under standard conditions) as a function of the temperature.

In the course of the reaction, the aluminosilicate gel is converted to a crystalline aluminosilicate. If the temperature of the reaction batch is higher than 190° C., the growth of the aluminosilicate primary crystallites becomes too fast, and primary crystallites of a diameter of more than 0.9 micron are obtained, while simultaneously aluminosilicate gel is still present in the reaction batch.

The templates used are tetraalkylammonium compounds, wherein each alkyl group contains about 1 to about 5 carbon atoms. Preferred templates are tetrapropylammonium hydroxide (TPAOH) or tetrapropylammonium halides e.g., bromides (TPABr). Mixtures of ammonia or an organic amine e.g., a mono, di, or trialkyl amine having 1 to 5 carbon atoms in each alkyl group and one to five carbon alcohols, preferably butanol, can also be used as templates.

The aqueous reaction batch of stage (a) has preferably a pH value from 10 to 13. At a pH value of less than 10, the conversion of the aluminosilicate gel into crystalline aluminosilicate proceeds relatively slowly. At pH values higher than 13, the aluminosilicate crystals can redissolve in some cases. In general, however, this can be tolerated, because as a rule only the smaller primary crystallites having a diameter of less than 0.1 micron redissolve initially.

The formation of the crystalline aluminosilicate primary crystallites can be controlled by a suitable selection of the source of silicon, the source of aluminum, the source of alkali and the template, and by a suitable selection of the temperature, the pH value and the stirrer speed. The essential point is that the reaction is stopped when the primary crystallites obtained have a mean diameter of at least about 0.1 micron and at most about 0.9 micron.

For this purpose, several test batches are carried out. After just a few experiments, the optimum parameters can be found, as a result of which the required size regions of the primary crystallites are reached. Another indication of the end of the reaction is an abrupt rise in the pH value of the reaction batch.

According to the invention, it is not necessary to prepare a new reaction batch in every case. Rather, the source of silicon, the source of alkali, the source of aluminum, the template and the water from the mother liquors of previous syntheses can be used for producing the aluminosilicate gel and be made up by the quantities, required for the synthesis of the aluminosilicate gel, of the said compounds.

The formation of the aluminosilicate primary crystallites of stage (a) takes place preferably at a pH value between 10 and 13, the reaction batch being stirred. The size distribution of the primary crystallites is homogenized in this way. However, the stirrer speed should preferably be not more than about 900 rpm. At higher stirrer speeds, the fraction of smaller primary crystallites is higher, so that the reaction time must be extended in order to ensure that the mean diameter of all the primary crystallites is at least about 0.1 micron.

In stage (b), the primary crystallites are separated as pre-agglomerates from the aqueous reaction medium, i.e., not as individual crystallites. This is preferably achieved by adding a flocculant to the aqueous reaction medium. In general, the flocculant used is a cationic organic macromolecular compound, preferably a copolymer of acrylamide and a cationic acrylic acid derivative.

The flocculant not only facilitates the separation of the primary crystallites from the reaction medium (improved filterability), but also has the effect that the primary crystallites combine into pre-agglomerates which, with respect to size, structure and association of the primary crystallites, already largely resemble the agglomerates formed in the next stage. The pre-agglomerates are dried and subjected to an intermediate calcination which is initially carried out preferably in an inert atmosphere at about 200° to 350° C., in particular at about 250° C., with part of the template remaining in the crystallites.

The intermediate calcination can be completed in an oxidizing atmosphere at about 500° to 600° C., any residual quantity of template, which may still be present, being burned off.

In general, the pre-agglomerates are subjected to the intermediate calcination for about 1 to about 20 hours in the inert atmosphere and for about 1 to 30 hours in the oxidizing atmosphere.

In stage (c), the product from stage (b) is reacted in an aqueous medium with a substance containing protons or donating protons on heating, for the purpose of exchanging the alkali metal ions. For example, the ion exchange can be carried out by means of a dilute mineral acid (for example hydrochloric acid or sulfuric acid) or an organic acid (for example acetic acid). The ion exchange preferably takes place with stirring for at least one hour at temperatures between 25° and 100° C., at least a part of the alkali metal ions in the pre-agglomerates of the primary crystallites being exchanged for hydrogen ions. If necessary, the ion exchange can be repeated under the same conditions.

After the exchange of the alkali metal ions in the aqueous medium, the product containing protons (H zeolite) is separated off (for example by filtration), dried and subjected again to an intermediate calcination. The intermediate calcination is carried out at temperatures from 400° to 800° C., preferably at about 550° C. to about 650° C. for a period of about 5 to 20 hours.

The ion exchange can also be carried out by means of an ammonium salt solution under comparable conditions, instead of using the dilute acid. In this case, the alkali metal ions are exchanged for ammonium ions. When the product thus obtained is subjected to intermediate calcination, ammonia is removed, and a product containing protons is obtained.

The product obtained after the intermediate calcination contains, on the one hand, agglomerates of $\geq 500$ microns and on the other hand dust fractions of $\leq 5$ microns. Thus, an agglomerate fraction from about 5 to 500 microns is separated off.

This agglomerate fraction is mixed in stage (d) with the finely divided hydrated alumina, of which at least 95 percent are $\leq 55$ microns and at least 30 percent are $\geq 35$ microns. These values are averaged over a large number of crystallites, in each case relative to the mean diameter which is defined as the mean diameter of the primary crystallites. In detail, the alumina typically has the following grain size spectrum:

99 percent $\leq 90$ microns
95 percent $\leq 45$ microns
55 percent $\leq 25$ microns The hydrated alumina is essentially responsible for setting the pore volume of the catalyst according to the invention. The quantity of the finely divided hydrated alumina binder preferably amounts to about 10 to 70 percent by weight, relative to the total weight of the product from stage (d). Preferably, the finely divided hydrated alumina binder is a peptizable alumina which is particularly low in Na and Fe.

The peptization is preferably carried out with a highly dilute weak acid, for example in 1.5 percent acetic acid.

The product from stage (d) is subjected to a final calcination. This can be carried out at temperatures from about 400° to 800° C., preferably at about 525° C. to about 575° C., for a period from 5 to 20 hours.

The end product thus obtained can be used in methanol conversion processes for the production of olefins and/or gasoline or for the production of gasoline and/or diesel fuels from low-molecular olefins or low molecular organic oxygen compounds, including lower alcohols, such as methanol or ethanol, and dimethyl ether.

The invention is explained in more detail by the examples which follow.

COMPARATIVE EXAMPLES 1 and 2

The reaction mixture was prepared by intensive mixing of two solutions at room temperature in a 40 liter autoclave. The two solutions were designated as solution A and solution B. Solution A was prepared by dissolving 554 g of tetrapropylammonium bromide (TPABr) in 11 kg of deionized water. 2500 g of commercially available silica were introduced into this solution. Solution B was prepared by dissolving 183 g of NaOH (Example 2: 116.5 NaOH) and subsequently 34.1 g of NaAlO$_2$ in 5.5 liters of deionized water. Solution B, while still warm, was added to solution A. The autoclave was then sealed and immediately brought to the reaction temperature with stirring at about 60 rpm. After about 137 hours (Example 2: 240 hours), the reaction was complete as could be seen from the abrupt pH change (from 11.4 to 12.0). After cooling, the autoclave was opened, and the product was removed from the reaction vessel and filtered. The readily filterable filter cake was washed until the pH value was 7 to 8 and until the Br concentration in the washing water was less than 1 ppm, and calcined for 24 hours at 540° C. The size of the primary crystallites is indicated in Table I. The conditions required to obtain the desired crystallite sizes had been determined beforehand in a series of experiments.

In these comparative examples, the reaction was deliberately carried out for a very long time, in order to obtain larger primary crystallites.

The calcined Na zeolite was suspended in 5 times the quantity of a 1-molar aqueous HCl solution and brought to 80° C. The mixture was stirred for one hour at this temperature.

The H zeolite was washed until the chloride content in the washing water was less than 5 ppm. The dried H zeolite was comminuted to 2 mm by means of a commercial granulator and brought in air to 540° C. at a heating rate of 1° C./minute and calcined in air at this temperature for 10 hours. The physical and chemical properties of the calcined zeolite in the proton form (H zeolite) are indicated in Table I.

5000 g of the calcined H zeolite were ground in a laboratory mill. The particle size spectrum of the ground zeolite was as follows:

0.2 percent by weight >500 microns
20 percent by weight =200 to 500 microns
39 percent by weight =100 to 200 microns
23 percent by weight =40 to 100 microns
17 percent by weight <40 microns The ground zeolite was mixed dry for 15 minutes in a kneader with 1250 g of a calcium bentonite having the following particle size distribution.

98 percent by weight ≦150 microns
88 percent by weight ≦73 microns
80 percent by weight ≦60 microns About 190 ml of steatite oil (to facilitate kneading) and 3770 ml of water were added slowly to this mixture. This mixture was kneaded for about 30 minutes until plasticization was obtained. By means of an extruder, the mixture was extruded to give moldings of a diameter from about 1.5 mm to about 3.2 mm and a length from about 2 mm to about 6 mm. The analytical results are indicated in Table I.

COMPARATIVE EXAMPLE 3

According to this example, aluminosilicate zeolites having a primary crystallite size of ≦1 micron were prepared. The catalysts were produced with an addition of bentonite as a binder. In detail, the procedure was as follows:

A reaction mixture was prepared by intimate mixing of two solutions at room temperature in a 40 liter autoclave. The two solutions were designated as solution A and solution B. Solution A was prepared by dissolving 2218 g of TPABr in 11 kg of deionized water. 5000 g of commercially available silica were introduced into this solution. Solution B was prepared by dissolving 766 g of NaOH and subsequently 45.6 g of Na AlO$_2$ in 5.5 liters of deionized water. While still warm, solution B was added to solution A. The autoclave was then sealed and immediately brought to the reaction temperature with stirring at about 60 rpm. After about 50 hours, the reaction was complete as could be seen from the abrupt change in pH. After cooling, the autoclave was opened, and the product was removed from the reaction vessel and filtered. The filter cake was suspended in about 40 liters of deionized water, about 5 liters of a 0.4 percent by weight aqueous suspension of a commercially available cationic flocculant (Praestol BC 11L, a copolymer of acrylamide and a cationic acrylic acid derivative) were added and, after stirring and settling of the pre-agglomerates of the solid, the liquid was decanted. The washing process described was repeated until the washing water had a pH value from 7 to 8 and a Br concentration of less than 1 ppm. The suspension, in which pre-agglomerates of primary crystallites were visible, which were evidently held together by the flocculant, was filtered in the manner indicated in comparative examples 1 and 2. The filter cake was then dried for 12 hours at 120° C.

The dried filter cake was comminuted to a particle size of 2 mm by means of a commercially available granulator.

The granules were brought under nitrogen (1000 l (S.T.P.)/hour) at a heating rate of 1° C./minute to 350° C. and calcined for 15 hours at 350° C. under nitrogen (1000 l (S.T.P.)/hour). The temperature was then raised to 540° C. at a heating rate of 1° C./minute, and the granules were calcined in air for 24 hours at this temperature, in order to burn off the remaining TPABr. The calcined Na zeolite was analyzed, the results indicated in Table I being obtained.

The calcined Na zeolite was suspended in 5 times the quantity of a 1-molar aqueous HCl solution and brought to 80° C. The mixture was stirred for 1 hour at this temperature. About 1 liter of a 0.4 percent by weight suspension of the cationic flocculant of Example 1 was then added, and the supernatant acid was decanted off after settling of the solid. The procedure thus described was repeated once more.

The solid was suspended with stirring in 60 liters of deionized water in each of about 10 washing procedures, and on average 100 ml of a 0.4 percent by weight suspension of the flocculant were added. After settling of the zeolite, the supernatant solution was decanted off. When the Cl content in the washing water was <5 ppm, the suspension was filtered and the filter cake was dried for 15 hours at 120° C.

The dried H zeolite was comminuted to 2 mm by means of a commercially available granulator and brought in air to 540° C. at a heating rate of 1° C./minute and calcined in air for 10 hours at this temperature. The specification of this calcined H zeolite is indicated in Table I.

5000 g of the calcined H zeolite were ground in a laboratory mill to a particle size of 500 microns and mixed dry for 15 minutes in a kneader with 1250 g of a calcium bentonite having a particle size spectrum of 98 percent by weight ≦150 microns
88 percent by weight ≦75 microns
80 percent by weight ≦60 microns 190 ml of steatite oil and 3770 ml of water were added slowly to this mixture. This mixture was kneaded for about 30 minutes until plasticized. The sample was extruded by means of an extruder to give moldings of a diameter of about 3.2 mm and a length of about 6 mm.

The results of the analysis of the product are indicated in Table I.

EXAMPLE 1

The aluminosilicate crystals are prepared as described in Comparative Example 3. The calcination and the ion exchange also took place in accordance with Comparative Example 3.

5000 g of a calcined H zeolite were ground to a particle size of about 500 microns by means of a laboratory mill and mixed dry for 15 minutes in a double-Z kneader with 1470 g of a commercially available peptizable hydrated alumina having a particle size spectrum of 99 percent by weight $\leq$ 90 microns
95 percent by weight $\leq$ 45 microns
55 percent by weight $\leq$ 25 microns 4565 ml of a 1.5 percent by weight aqueous acetic acid solution (for peptizing the hydrated alumina) and 417 ml of steatite oil were slowly added to this mixture.

This mixture was then kneaded for about 30 minutes until plasticized and extruded in a commercially available extruder to give moldings of a diameter of about 1.6 mm and a length of about 2–6 mm. The final calcination was carried out for 3 hours at 650° C.

The analytical values and the physical and chemical properties of the product are indicated in Table II.

EXAMPLE 2

The reaction mixture was prepared by intimate mixing of two solutions at room temperature in a 40 liter autoclave. The two solutions were designated as solution A and solution B. Solution A was prepared by dissolving 2218 g of TPABr in 11 kg of deionized water. 5000 g of a commercially available silica were introduced into this solution. Solution B was prepared by dissolving 766 g of NaOH and subsequently 136.6 g of NaAlO$_2$ with stirring in 5.5 liters of deionized water. While still warm, solution B was added to solution A. The autoclave was then sealed and immediately brought to the reaction temperature of 130° C. with stirring at about 60 rpm. After about 60 hours at 130° C. with stirring at 60 rpm, the reaction was completed, as could be seen from the abrupt pH change from 11.4 to 12.3 and the subsequent constancy of the pH value. After cooling, the autoclave was opened, and the product was removed from the reaction vessel and filtered. At the same time, the size of the primary crystallites was determined (compare Table II). The filter cake was suspended in about 40 liters of deionized water, about 5 liters of a 0.4 percent by weight aqueous suspension of a flocculant (Praestol BC 11L, a copolymer of acrylamide and a cationic acrylic acid derivative) were added, and after stirring and settling of the solid, the liquid was decanted. The washing procedure described was continued until a pH value of 7 to 8 and a Br concentration in the washing water of less than 1 ppm were reached. The solid was then filtered off, as described above. The filter cake was then dried for 12 hours at 120° C.

The catalysts was prepared as according to Example 1. The size of the primary crystallites and the chemical and physical properties of the catalyst are indicated in Table II.

EXAMPLE 3

A reaction mixture was prepared by intimate mixing of two solutions at room temperature in a 40 liter autoclave. The two solutions were designated as solution A and solution B. Solution A was prepared by mixing about 1.92 kg of deionized water with 2.537 liters of a 20 percent by weight aqueous solution of tetrapropylammonium hydroxide (TPAOH). 1500 g of a commercially available silica were introduced into this solution. Solution B was prepared by dissolving 120 g of NaOH and then 14.2 g of NaAlO$_2$ in 1 liter of deionized water. While still warm, solution B was added to solution A. The autoclave was then sealed and immediately brought to 130° C. with stirring at about 60 rpm. After about 24 hours at 130° C., the reaction was complete, as could be seen from the abrupt change in pH. After cooling, the autoclave was opened, and the product was removed from the reaction vessel and filtered. The filter cake was, as described in Example 2, washed, calcined and worked up to give the finished catalyst. The size of the primary crystallites and the chemical and physical properties of the catalyst are indicated in Table II.

EXAMPLE 4

The reaction mixture was prepared by intimate mixing of two solutions at room temperature in a 40 liter autoclave. The two solutions were designated as solution A and solution B. Solution A was prepared by mixing 988 g of butanol and 266 g of a 25 percent NH$_3$ solution with 10 kg of H$_2$O. Solution B was prepared by dissolving 160 g of NaOH in about 2 kg of deionized water. 36.3 g of NaAlO$_2$ were introduced into this solution. Solution A was added to solution B, and 2000 g of a commercially available silica were introduced with stirring into this mixture. The autoclave was then sealed and immediately brought to the reaction temperature of 180° C. with stirring at about 64 rpm. After about 34 hours, the reaction was complete, as could be seen from the abrupt change in pH. After cooling, the autoclave was opened, and the product was removed from the reaction vessel and filtered. The filter cake was worked up to give the finished catalyst by the procedure described in Example 2. The size of the primary crystallites and the physical and chemical properties of the catalyst are indicated in Table II.

TABLE I

| Comparative Example | 1 | 2 | 3 |
|---|---|---|---|
| Molar ratio of the starting materials | | | |
| SiO$_2$ | 100 | 100 | 100 |
| NaAlO$_2$ | 1 | 1 | 0.67 |
| NaOH | 11 | 7 | 23 |
| TPABr | 5 | 5 | 10 |
| H$_2$O | 2200 | 2200 | 1100 |
| Crystallization data | | | |
| Temperature (°C.) | 130 | 130 | 130 |
| Time (hours) | 137 | 240 | 50 |
| Si and Al contents of the unit cell of the Na zeolite | | | |
| Si | 95.14 | 95.22 | 94.98 |
| Al | 0.86 | 0.77 | 1.02 |
| Si/Al | 111.26 | 123 | 93 |
| Physical and chemical properties of the calcined zeolite in the proton form | | | |
| Si/Al | 130 | 130 | 84 |
| Crystallinity (%) | 100 | 100 | 100 |
| Primary crystallite size (microns) | 2.75 | 4.5 | 0.4 |
| BET surface area (m$^2$/g) | 318 | 345 | 320 |
| Pore volume (cm$^3$/g) | 0.38 | 0.45 | 0.52 |
| Pores greater than 80 nm (%) | 91.4 | 72.5 | 78.8 |
| Pores 14–80 nm (%) | 4.3 | 14.6 | 15.9 |

TABLE II

| Example | 1 | 2 | 3 | 4 |
|---|---|---|---|---|
| Molar ratio of the starting materials | | | | |
| SiO$_2$ | 100 | 100 | 100 | 100 |
| NaAlO$_2$ | 0.67 | 2 | 0.67 | 1.33 |
| NaOH | 23 | 23 | 12 | 12 |

TABLE II-continued

| Example | 1 | 2 | 3 | 4 |
|---|---|---|---|---|
| TPABr | 10 | 10 | | |
| TPAOH | | | 10 | |
| (0.4 BuOH, 0.1 NH$_3$) | | | | 100 |
| H$_2$O | 1100 | 1100 | 1100 | 2000 |
| *Crystallization data* | | | | |
| Temperature (°C.) | 130 | 130 | 130 | 180 |
| Time (hours) | 50 | 60 | 24 | 34 |
| Crystallinity (%) | 100 | 100 | 100 | 100 |
| Primary crystallite size (microns) | 0.3 | 0.3 | 0.3 | 0.5 |
| *Si and Al contents of the unit cell of the Na zeolite* | | | | |
| Si | 95.04 | 93.6 | 95.04 | 94.61 |
| Al | 0.953 | 1.03 | 0.96 | 1.39 |
| Si/Al | 99.7 | 39.07 | 99 | 66 |
| *Physical and chemical properties of the catalyst* | | | | |
| Si/Al | 105 | 41 | 104 | 70 |
| BET surface area (m$^2$/g) | 366 | 370 | 375 | 365 |
| Pore volume (cm$^3$/g) | 0.51 | 0.6 | 0.55 | 0.45 |
| Pores ≧80 nm (%) | 21.1 | 8.6 | 10.0 | 15.0 |
| Pores 14–80 nm (%) | 68.0 | 76.5 | 61.0 | 63.0 |

EXAMPLE 5

A reaction mixture was prepared by intimate mixing of two solutions at room temperature in a 40 liter autoclave. The two solutions were designated as solution A and solution B. Solution A was prepared by dissolving 2218 g of TPABr in 11 kg of deionized water. 5000 g of a commercially available silic acid (SiO$_2$ x 0.45 H$_2$O) were introduced into this solution. Solution B was prepared by dissolving 766 g of NaOH and then 45.6 g of NaAlO$_2$ in 5.5 liters of deionized water with stirring. While still warm, solution B was added to solution A. The autoclave was then sealed and immediately brought to the reaction temperature of 130° C. with stirring at about 60 rpm. After about 70 hours at 130° C., the reaction was complete, as could be seen from the abrupt change in pH. After cooling, the autoclave was opened, and the product was removed from the reaction vessel and filtered. The physical and chemical properties are indicated in Table III.

The mother liquor (9 liters) contained 0.69 mol/liter of OH−, 2 mg/liter of Al, 62.7 g/liter of C (from the template), 35 g/liter of Si and 51.1 g/liter of Br− (from the template).

The second batch of the same molar composition was prepared by intimate mixing of two solutions at room temperature in a 40 liter autoclave. The two solutions were designated as solution C and solution D. Solution C was prepared by dissolving 520 g of NaOH and 45.6 g of NaAlO$_2$ in 9 kg of deionized water. 1043 g of TPABr were added to this solution. For solution D, the mother liquor from the first batch was used. Solution D was added to solution C. 5000 g of commercially available silica were introduced into this mixture. The autoclave was then sealed and immediately brought to 130° C. with stirring at about 60 rpm. After about 72 hours, the reaction was complete, as could be seen from the abrupt change in pH. After cooling, the autoclave was opened, and the product was removed from the reaction vessel and filtered.

For the further cycles, the corresponding procedure was used, allowing for the particular composition of the mother liquor. The filter cake was washed until the pH value was 7 to 8 and until the Br concentration in the washing water was less than 1 ppm, with addition of a flocculant as described in Comparative Example 3, and calcined for 24 hours at 540° C.

The catalyst was finished by the process described in Example 1. The results are indicated in Table III.

TABLE III

| Example 5 | Synthesis | 1st Recycle | 5th Recycle |
|---|---|---|---|
| *Molar ratio of the starting materials (SiO$_2$ base)* | | | |
| SiO$_2$ | 100 | 100 | 100 |
| NaAlO$_2$ | 0.76 | 0.67 | 0.67 |
| NaOH | 26.1 | 23 | 23.1 |
| TPABr | 11.3 | 10 | 10 |
| H$_2$O | 1300 | 1250 | 1250 |
| *Crystallization data* | | | |
| Temperature (°C.) | 130 | 130 | 130 |
| Time (hours) | 72 | 72 | 72 |
| Stirring (rpm) | 63 | 60 | 60 |
| Crystallinity (%) | 100 | 100 | 100 |
| Primary crystallite size (microns) | 0.2–0.8 | 0.2–0.8 | 0.2–0.8 |
| *Si and Al contents of the unit cell of the Na zeolite* | | | |
| Si | 95.17 | 95.24 | 95.22 |
| Al | 0.83 | 0.76 | 0.78 |
| Si/Al | 114 | 125 | 122 |
| *Physical and chemical properties of the catalyst* | | | |
| Si/Al | 100 | 100 | 100 |
| BET surface area (m$^2$/g) | 360 | 355 | 363 |
| Pore volume (cm$^3$/g) | 0.49 | 0.53 | 0.48 |
| Pores ≧80 nm (%) | 14 | 7 | 13 |
| Pores 14–80 nm (%) | 62 | 67 | 65 |

APPLICATION EXAMPLE 1

This application example shows, by reference to catalyst data of the CMO process (Conversion of Methanol to Olefins) in an isothermal fixed-bed reactor, the improvement achievable according to the invention by the use of the hydrated alumina binder and the pore radius distribution arising from the latter.

In detail, the tests were carried out as follows:

The methanol/water feed (1 g/1 g) was passed at an LHSV of 1(1/(1×h), i.e. liters of total feed per liter of catalyst and per hour, at a pressure of 1 bar, after passing through an isothermal fixed-bed tube reactor for partial conversion of methanol to dimethyl ether, passed over 300 cm$^3$ of CMO catalyst in an isothermal fixed-bed tube reactor. The conversion of the methanol was held at almost 100 percent. At a certain value (EOR conversion, %), the reaction was stopped and the catalyst was regenerated.

The gas phase and liquid phase at the exit of the CMO catalyst reactor were determined by the conventional gas-chromatographic analytical methods. The distribution of the hydrocarbons is summarized in Table IV, together with other relevant data.

TABLE IV

| Catalyst | Comparative Example 1 | Comparative Example 3 | Example 1 |
|---|---|---|---|
| Binder | Bentonite | Bentonite | Alumina |
| Primary crystallites (microns) | 2–3.5 | 0.3 | 0.3 |
| Temperature (°C.) | 415 | 415 | 400 |
| Pressure (bar) | 1 | 1 | 1 |
| LHSV (1/(1 × h) | 1 | 1 | 1 |
| MeOH/H$_2$O(g/g) | 1 | 1 | 1 |

TABLE IV-continued

| Catalyst | Comparative Example 1 | Comparative Example 3 | Example 1 |
|---|---|---|---|
| Duration of 1st cycle (hours) | 197 | 554 | 927 |
| Duration of 2nd cycle (hours) | 62 | 404 | 2000 |
| 1st cycle, averages % by weight | 10.6 | 9.44 | 10.5 |
| $C_1$-$C_4$ paraffins | 56.5 | 56.6 | 51.9 |
| $C_2$-$C_4$ olefins | 32.8 | 33.9 | 37.6 |
| EOR conversion, % | 96.2 | 97.1 | 99.7 |
| 2nd cycle, averages % by weight | | | |
| $C_1$-$C_4$ paraffins | 10.5 | 6.68 | 7.48 |
| $C_2$-$C_4$ olefins | 56.2 | 58.7 | 54.76 |
| $C_5+$ gasoline | 33.2 | 34.6 | 37.76 |
| EOR conversion, % | 99.97 | 97.1 | 100 stopped |

Table IV clearly shows the increased service life of the catalyst according to the invention from Example 1. With the catalyst according to Comparative Examples 1 and 3, the first cycle was stopped after the conversion at the end of the run (EOR) had reached 96.2 and 97.1 percent respectively. It is not meaningful to continue the cycle, since lower conversions are of no industrial interest. The catalysts (also the catalyst according to the invention) were regenerated after the end of the first cycle by first shutting off the MeOH stream. Nitrogen was then fed for displacing the residual MeOH. Finally, oxygen was slowly added in gradually increasing concentrations to the nitrogen, in order to burn off the carbon deposited on the catalysts. During this, the temperature of the catalysts was always kept below 480° C. The regeneration of the catalysts was complete when the oxygen content of the nitrogen stream was the same at the inlet and at the exit of the catalyst bed.

It is also to be noted that the catalyst according to Example 1 shows higher conversion values at 400° C. than the comparative catalysts which were tested at 415° C.

APPLICATION EXAMPLE 2

This example shows, by reference to catalyst data of the COD process (Conversion of Olefins to Diesel) in an isothermal fixed-bed reactor, the improvement achievable with the catalyst according to the invention by the use of the alumina binder and the pore radius distribution arising from the latter.

In detail, the tests were carried out as follows:

The 1:1 propane/butene feed was, in the case of the catalyst according to Comparative Example 3 without additional octene, passed under the conditions indicated the quantity of catalyst indicated in Table V in an isothermal fixed-bed tube reactor over the quantity of catalyst indicated in Table V. The loading was approximately the same at about 0.5 kg of propene/ketone per kg of catalyst and per hour.

If it is remembered that octene is fairly unreactive as compared with propene/butene, the result shows that the catalyst according to Example 1 with the alumina binder is significantly better with respect to selectivity and conversion than the catalyst according to Comparative Example 3 with bentonite as the binder, even though the primary crystallites of the zeolite component of both catalysts are of the same order of size.

TABLE V

| Catalyst | Comparative Example 3 | Example 1 |
|---|---|---|
| Binder | Bentonite | Hydrated alumina |
| Primary crystals (microns) | 0.3 | 0.3 |
| Temperature (°C.) | 301 | 300 |
| Pressure (bar) | 50 | 50 |
| Catalyst (g) | 83 | 86.4 |
| Olefin feed (g/h) | 38 | 45 (propene/butene-1 = 1:1) |
| Octene feed (g/h) | 0 | 45 |
| Olefin conversion (%) | 40.96 | 67.7 |
| $C_{11}+$ formation | 0.0177 | 0.5437 |
| Cycles | 2 | 1 |
| Running time in the cycle (hours) | 347 | 451 |

What is claimed is:

1. A catalyst based on crystalline aluminosilicates of the pentasil type, having an Si/Al atomic ratio of at least 10, said catalyst having a structure of primary crystallites of a mean diameter of about 0.1 micron to about 0.9 micron, wherein at least 20 percent of said crystallites are combined into agglomerates of about 5 to about 500 microns in size, the primary crystallites and agglomerates being mutually joined by finely divided alumina obtainable by hydrolysis of aluminum-organic compounds, wherein at least 95 percent (relative to the mean diameter) of the alumina particles being $\leq 55$ microns in size, wherein the BET surface area of the catalyst is about 300 to about 600 m²/g, wherein the pore volume (determined by mercury porosity) is about 0.3 to about 0.8 cm³/g and wherein at least 60 percent of the pores have a diameter of about 14 to about 80 nm.

2. The catalyst of claim 1, wherein the mean diameter of the primary crystallites is about 0.1 to about 0.6 micron.

3. The catalyst of claim 1 wherein the finely divided alumina binder is present in the amount of about 10 to about 40 percent by weight relative to the weight of the end product catalyst.

4. The catalyst of claim 1 wherein the finely divided alumina binder is in the form of peptizable hydrated alumina.

5. The catalyst of claim 1 wherein the finely divided alumina binder is obtained by hydrolysis of aluminum trialkyls or aluminum alkoxides.

6. In a process for preparing the catalyst of claim 1 by the elevated temperature reaction in an aqueous medium of colloidal silica or alkali metal silicate, aluminum hydroxide or alkali metal aluminate, a source of alkali and a template to form an alkaline aluminosilicate gel with subsequent conversion to a crystalline aluminosilicate, the improvement which comprises:
   a) stopping the reaction when the primary crystallites have a mean diameter of about 0.1 to about 0.9 micron;
   b) separating the primary crystallites as pre-agglomerates from the aqueous reaction medium;
   c) drying the crystallites and subjecting them to an intermediate calcination;
   d) reacting the product of step (c) in an aqueous medium a substance containing protons or donating protons on heating;
   e) separating and drying the crystallites and subjecting them to intermediate calcination;

f) separating out the agglomerates having a particle size of about 5 to about 500 microns;

g) mixing the separated agglomerates of step (f) with finely divided alumina; and h) subjecting the product of step (g) to final calcination.

7. The process of claim 6 wherein the substance containing protons is an acid, and the substance donating protons or heating is an ammonium salt.

8. The process of claim 6 wherein the colloidal silica or alkali metal silicate, aluminum hydroxide or alkali metal aluminate, the source of alkali, the template and the water from the mother liquor of previous synthesis are used for producing the aluminosilicate gel and made up by the quantities required by the synthesis of the aluminosilicate gel of the said compounds.

9. The process of claim 6 wherein the template is tetrapropyl ammonium hydroxide or tetrapropyl ammonium bromide.

10. The process of claim 6 wherein the template is a mixture of ammonia or an organic amine in an alcohol.

11. The process of claim 10 wherein the alcohol is butanol.

12. The process of claim 6 wherein the aqueous medium (first occurrence) has a pH of about 10 to about 13, and the formation of the primary aluminosilicate crystallites takes place with stirring at about 90° C. to about 190° C.

13. The process of claim 12 wherein the temperature is about 90° C. to about 150° C.

14. The process of claim 12 wherein the stirring is conducted at a maximum speed of 900 rpm.

15. The process of claim 6 wherein the primary crystallites are separated in step (b) with the addition of a flocculant.

16. The process of claim 15 wherein the flocculant is a cationic organic macromolecular compound.

17. The process of claim 16 wherein the flocculant is a copolymer of acrylamide and a cationic acrylic acid derivative.

18. The process of claim 6 wherein the intermediate calcination step (c) is conducted in an inert atmosphere at about 200° C. to about 350° C. and then in an oxidizing atmosphere at about 500° C. to about 600° C.

19. The process of claim 6 wherein the intermediate calcination of step (e) and the final calcination of step (h) is conducted at temperature of about 400° C. to about 800° C. for about 5 to about 20 hours.

* * * * *